United States Patent
Thornton

Patent Number: 5,846,082
Date of Patent: Dec. 8, 1998

[54] SYSTEM AND METHOD FOR CUSTOMIZING A DENTAL DEVICE USING AN IMPROVED DEFORMABLE MATERIAL

[76] Inventor: W. Keith Thornton, 5524 Edlen, Dallas, Tex. 75220

[21] Appl. No.: 695,862

[22] Filed: Aug. 5, 1996

Related U.S. Application Data

[63] Continuation-in-part of Ser. No. 653,285, May 24, 1996.

[51] Int. Cl.$^6$ ..................................................... A61C 5/00
[52] U.S. Cl. .............................................. 433/215; 433/48
[58] Field of Search ................................ 433/48, 90, 32, 433/214, 215

[56] References Cited

U.S. PATENT DOCUMENTS

| | | | |
|---|---|---|---|
| 2,505,028 | 4/1950 | Boeger | 433/90 |
| 3,064,354 | 11/1962 | Pos | 433/214 |
| 3,690,004 | 9/1972 | Frush | 433/214 |
| 3,882,601 | 5/1975 | Jahn | 433/214 |
| 4,227,877 | 10/1980 | Tureaud et al. | 433/37 |
| 4,784,123 | 11/1988 | Robeson | 128/90 |
| 5,011,407 | 4/1991 | Pelerin | 433/48 |
| 5,066,231 | 11/1991 | Oxman et al. | 433/48 |
| 5,112,225 | 5/1992 | Diesso | 433/48 |
| 5,190,457 | 3/1993 | Schreinemakers | 433/214 |
| 5,320,533 | 6/1994 | Lee | 433/215 |
| 5,370,533 | 12/1994 | Bushnell | 433/36 |
| 5,503,552 | 4/1996 | Diesso | 433/48 |
| 5,551,872 | 9/1996 | Mena | 433/37 |
| 5,562,449 | 10/1996 | Jacobs et al. | 433/215 |
| 5,582,517 | 12/1996 | Adell | 433/6 |

FOREIGN PATENT DOCUMENTS

WO9112777  9/1991  WIPO .

OTHER PUBLICATIONS

"Biodegradable Plastic Resins," Union Carbide Corporation Publication

*Primary Examiner*—Cary E. O'Connor
*Attorney, Agent, or Firm*—Baker & Botts, L.L.P.

[57] ABSTRACT

A system for customizing a dental device (10, 11) includes an arch (12, 14) operable to receive one or more of a user's teeth (16) and a deformable material (20, 32) that includes an aliphatic polyester. A delivery device (40) contains the deformable material (20, 32) and delivers at least some of the deformable material (20, 32) to a selected region of the arch (12, 14) to customize the dental device (10, 11) for the user. The aliphatic polyester may be a polycaprolactone polymer having the formula:

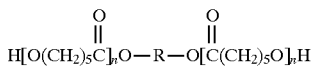

where R is an aliphatic hydrocarbon.

12 Claims, 2 Drawing Sheets

SYSTEM AND METHOD FOR CUSTOMIZING A DENTAL DEVICE USING AN IMPROVED DEFORMABLE MATERIAL

CROSS-REFERENCE TO RELATED APPLICATIONS

This application is a continuation-in-part of pending U.S. application Ser. No. 08/653,285, filed May 24, 1996, by W. Keith Thornton and entitled "Dental Device Having an Improved Deformable Material and Method for Forming Same."

This application is also related to pending U.S. application Ser. No. 08/621,133, filed Mar. 21, 1996, by W. Keith Thornton and entitled "Relined Dental Device and Method."

TECHNICAL FIELD OF THE INVENTION

This invention relates generally to dental devices, and more particularly to a system and method for customizing a dental device using an improved deformable material.

BACKGROUND OF THE INVENTION

Many dental devices include a deformable material for forming a mold of some or all of a user's teeth to customize the dental device for the user. It is often desirable to form a mold that properly fits the user's teeth to improve the performance of the associated dental device. Dental devices that do not properly fit the user's teeth may not adequately serve the purposes for which the devices are constructed.

As dental devices become increasingly complex to satisfy a variety of treatment, comfort, safety, and other requirements, users or clinical professionals may wish to form a mold that more optimally fits the user's teeth. A known technique for forming a mold of a user's teeth includes inserting a heat-deformable mouthpiece into the user's mouth, pressing the user's teeth into the mouthpiece, and removing the mouthpiece from the user's mouth after the mouthpiece has cooled. Such techniques may not provide a proper fit, however, due to the tendency of many deformable materials to contract during cooling, thereby expanding the impressions made by the user's teeth. In addition, this technique must often be repeated numerous times before even a marginally adequate fit can be achieved.

Deformable materials used in connection with such techniques may also cool more quickly and display less thermoplasticity at certain temperatures than the user or clinical professional might desire, thereby limiting the time in which the user or clinical professional may manipulate the deformable material to form a mold of the user's teeth. Furthermore, mouthpieces fitted using such techniques may be less safe for the user due to the increased tendency of the user's teeth to move with respect to a mouthpiece that does not properly fit the user's teeth. Moreover, many deformable mouthpiece materials may display insufficient dimensional stability during cooling, bonding properties, hardness, or biocompatibility to function properly in a variety of contexts. In addition, such materials may be difficult or impossible to introduce into the mouth of a user to properly customize an existing mouthpiece, limiting the efficiency, economic availability, and effectiveness of techniques associated with these materials.

SUMMARY OF THE INVENTION

In accordance with the present invention, the disadvantages and problems associated with systems and methods for customizing dental devices using deformable materials have been substantially reduced or eliminated.

In accordance with one embodiment of the present invention, a system for customizing a dental device includes an arch that receives one or more of a user's teeth and a deformable material that includes an aliphatic polyester. A delivery device contains the deformable material and delivers at least some of the deformable material to a selected region of the arch to customize the dental device for the user. In a more particular embodiment, the aliphatic polyester is a polycaprolactone polymer having the formula:

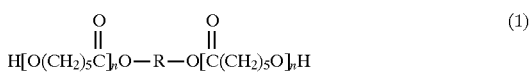

$$H[O(CH_2)_5C]_nO-R-O[C(CH_2)_5O]_nH \qquad (1)$$

where R is an aliphatic hydrocarbon.

Important technical advantages of the present invention include providing a system and method for customizing a dental device using an improved deformable material to more optimally fit a user's teeth. Improved fit may be important in connection with dental devices designed to reduce or eliminate trauma injuries or breathing problems such as sleep apnea. The present invention provides desirable hardness, biocompatibility, dimensional stability during cooling, thermoplasticity, and bonding properties for a variety of contexts. Furthermore, because it allows the improved deformable material to be delivered to a selected region, the present invention significantly improves the ability of users or clinical professionals to customize dental devices in an efficient, economically available, and effective manner. Other technical advantages are readily apparent to one skilled in the art from the following figures, descriptions, and claims.

BRIEF DESCRIPTION OF THE DRAWINGS

For a more complete understanding of the present invention and for further features and advantages thereof, reference is now made to the following description taken in conjunction with the accompanying drawings, in which.

DETAILED DESCRIPTION OF THE INVENTION

Figure 1A:
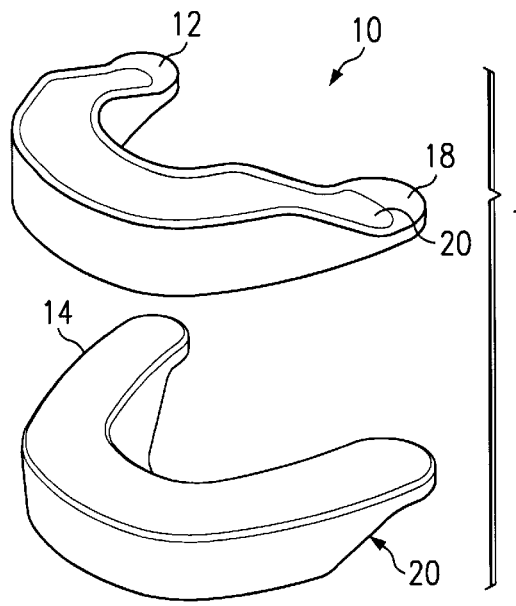
FIGS. 1a and 1b illustrate dental devices having an improved deformable material.

FIG. 1a illustrates a dental device 10 that includes an upper arch 12 adapted to receive one or more of a user's upper teeth and a lower arch 14 adapted to receive one or more of the user's lower teeth. When dental device 10 is in use or is being customized according to the present invention, upper arch 12, lower arch 14, or both upper arch 12 and lower arch 14 are inserted into the user's mouth. Although device 10 may include upper arch 12, lower arch 14, or both upper arch 12 and lower arch 14, device 10 is discussed below as including only upper arch 12. It should be understood that the following discussion applies equally to a device 10 that includes lower arch 14 instead of, or in addition to, upper arch 12.

Upper arch 12 includes a tray 18 formed from any material suitable for dental uses, for example, methyl methacrylate or a polycarbonate resin thermoplastic such as that sold under the Registered Trademark LEXAN. Such materials are known to those familiar with dental devices, and other suitable materials may be used to form tray 18 without departing from the intended scope of the present invention.

For example, tray 18 may also be formed from another thermoplastic polymer, such as a polycaprolactone polymer or other aliphatic polyester described in U.S. Pat. Nos. 5,112,225 and 4,784,123, both of which are herein incorporated by reference, as well as in literature distributed by Union Carbide Corporation. A polycaprolactone polymer may be combined with another polymer or other suitable material to form tray 18 having any number of characteristics, properties, or uses. The present invention contemplates using one or more polycaprolactone polymers or other suitable aliphatic polyesters to replace or combine with methyl methacrylate for any suitable dental application.

Tray 18 is adapted to receive a deformable material 20 in which molds of one or more of the user's upper teeth may be formed. In one embodiment, deformable material 20 includes a polycaprolactone polymer or other aliphatic polyester discussed above. The polycaprolactone polymer may have the formula:

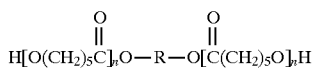 (2)

where R is an aliphatic hydrocarbon and n may range from approximately 300 to approximately 650. The present invention contemplates polycaprolactone polymers having other suitable formulas.

Deformable material 20 may include any suitable polycaprolactone polymer or other aliphatic polyester, for example, and not by way of limitation, the TONE P-700, TONE P-767, or TONE P-787 polycaprolactone polymers manufactured by Union Carbide Corporation, taken singly or in any combination. A suitable light cured material, another polymer, or any other suitable material, such as a filler, coloring agent, stabilizer, antioxidant, or antimicrobial agent, may be used to replace or combine with a polycaprolactone polymer in forming a deformable material 20 having any number of characteristics, properties, or uses.

The TONE polycaprolactone polymers are described in U.S. Pat. Nos. 5,112,225 and 4,784,123, and in literature distributed by Union Carbide Corporation, as homopolymers, block copolymers, graft copolymers, or other polymers that contain epsilon-caprolactone. Polymerization may be initiated using a diol, for example, and not by way of limitation, ethylene glycol, diethylene glycol, neopentyl glycol, butane diol, hexane diol, or any other suitable diol. The diol may have the formula:

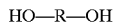 (3)

where R is an aliphatic hydrocarbon.

In one embodiment, deformable material 20 includes approximately thirty (30) parts by volume TONE P-700 and sixty (60) parts by volume TONE P-767, together with approximately ten (10) parts by volume of one or more other polymers, depending on the application. The present invention contemplates forming an impression material such as deformable material 20 using any suitable mixture or other combination of polycaprolactone polymers, other polymers, and other suitable materials, compounds, or compositions.

Deformable material 20 may begin as extruded pellets, beads, or rods of uniform, similar, or differing size, or in other suitable form. Deformable material 20 is heated in a microwave oven, in water or other non-solvent neutral liquid, or in any other suitable manner to between approximately 140 degrees Fahrenheit and approximately 180 degrees Fahrenheit to place deformable material 20 in its deformable state. Deformable material 20 may be kept in a deformable state until the pellets, beads, or rods congeal, coalesce, or otherwise combine to form a deformable mass capable of assuming a multitude of shapes and configurations. Deformable material 20 may be placed in a deformable state before, during, or after deformable material 20 is delivered to upper arch 12 or coupled to tray 18. The present invention contemplates deformable material 20 mixing, reacting, or otherwise combining with the material used to form tray 18 while deformable material 20 is in a liquid or other deformable state.

In one embodiment, upper arch 12, including tray 18 and deformable material 20, is inserted into the user's mouth separately from or together with lower arch 14. The user bites down or otherwise presses the user's teeth into deformable material 20 in order to form a mold of one or more of the user's teeth. Deformable material 20 is then allowed to cool and harden or otherwise take a more permanent shape. These steps may be repeated as many times as necessary or desired to form a mold of one or more of the user's teeth using deformable material 20. In another embodiment, tray 18 is inserted into the user's mouth to receive one or more of the user's teeth, and deformable material 20 is delivered to tray 18 or selected regions of tray 18 to form a mold of the user's teeth. Deformable material 20 may be delivered to tray 18 while in a liquid, melted, or other deformable state using a syringe, hypodermic needle, hot glue gun, or other suitable delivery device.

An important technical advantage of the present invention is that deformable material 20 may cool more slowly and may display thermoplastic properties at lower temperatures than materials such as the ethylene-vinyl acetate copolymer resin sold under the Registered Trademark ELVAX. This provides the user or clinical professional with more time to properly conform deformable material 20 to the user's teeth. In addition, deformable material 20 may display increased dimensional stability during the cooling process, relative to ELVAX, which may reduce or eliminate fitting problems that might otherwise develop due to the tendency of materials such as ELVAX to contract during cooling, thereby expanding the impressions made by the user's teeth. Furthermore, deformable material 20 may be more easily, efficiently, and economically applied than other deformable materials using an appropriate delivery device.

Upper arch 12 may remain inserted in the user's mouth or may be removed from the user's mouth before, during, or after deformable material 20 cools. Deformable material 20 may be formed into a mold of the user's teeth in the user's home, in the office of a clinical professional, or in any other suitable location. The present invention contemplates any suitable technique for forming a mold of one or more of the user's teeth using one or more polycaprolactone polymers. Furthermore, upper arch 12 may be coupled to lower arch 14, a mask, or other apparatus in some suitable manner to form a device suitable for preventing trauma injuries or treating breathing problems such as sleep apnea.

Figure 1B:
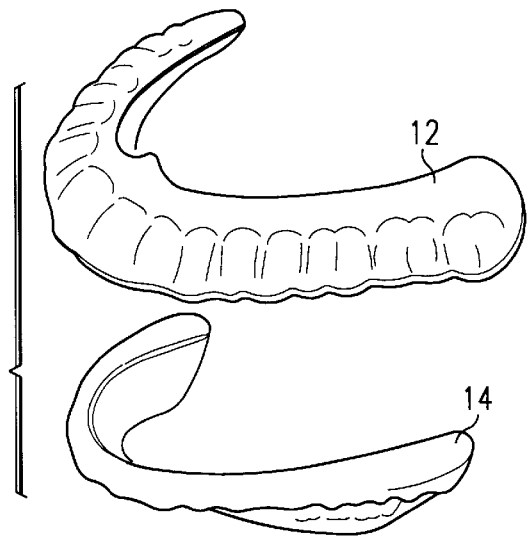

Alternatively, as shown in FIG. 1b, upper arch 12, lower arch 14, or both upper arch 12 and lower arch 14 may themselves be formed from a deformable material suitable for dental uses, for example, a deformable material that includes a polycaprolactone polymer or other aliphatic polyester discussed above. A suitable light cured material, another polymer, or any other suitable material may be used to replace or combine with a polycaprolactone polymer in forming the deformable material, depending on the application. Whether upper arch 12 and lower arch 14 are themselves formed using a polycaprolactone polymer or are formed so as to include a deformable material 20 that includes a polycaprolactone polymer, upper arch 12, lower arch 14, or both upper arch 12 and lower arch 14 may be relined using one or more polycaprolactone polymers to more optimally fit the user's teeth.

Figure 2A:
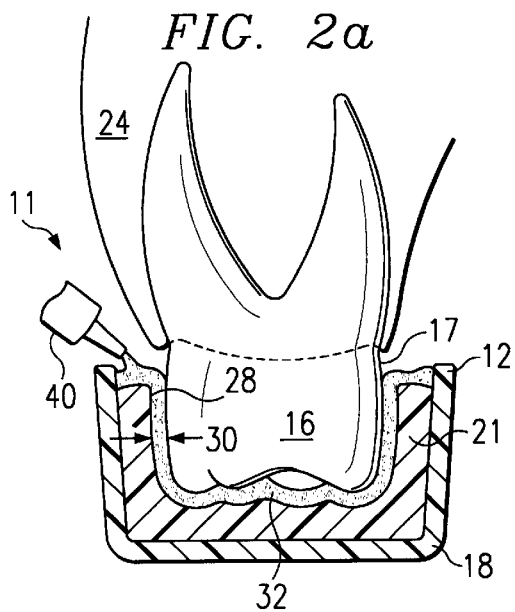
FIGS. 2a and 2b illustrate a method for customizing a dental device using an improved deformable material.
Figure 2B:
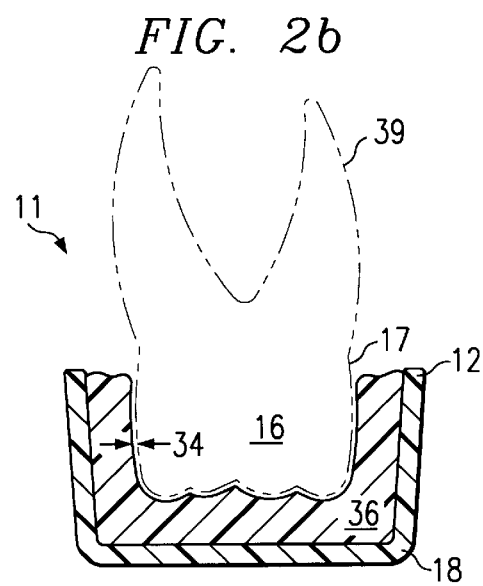

FIGS. 2a and 2b illustrate a method for relining a dental device 11 using one or more of the polycaprolactone polymers or other aliphatic polyesters discussed above with reference to FIGS. 1a and 1b. A suitable light cured material, another polymer, or any other suitable material may be used to replace or combine with the polycaprolactone polymers in relining dental device 11. Referring to FIG. 2a, one or more of the user's upper or lower teeth, represented generally by tooth 16, have been pressed or otherwise inserted into some suitable deformable material 21 to form a first mold 28 of tooth 16 that resembles the outward surface 17 of tooth 16. Although upper arch 12 is discussed as including first mold 28, the present invention contemplates device 11 having lower arch 14 instead of, or in addition to, upper arch 12.

Tooth 16 is shown in its natural state within the user's gum 24. Deformable material may include any material suitable for dental applications, for example, the ethylene vinyl copolymer resin sold under the Registered Trademark ELVAX or one of the polycaprolactone or other polymers discussed above. Deformable material 21 has been allowed to cool and harden or otherwise take a more permanent shape. Due to the tendency of materials such as ELVAX to contract during cooling, the impression made by the user's teeth may have expanded to form a first mold 28 that does not optimally fit the user's teeth. Alternatively, first mold 28 may have been improperly formed, such that first mold 28 does not optimally fit the user's teeth. First offset 30 indicates the amount by which first mold 28 is separated from outward surface 17 when tooth 16 is positioned within upper arch 12. The present invention further contemplates forming first mold 28 using the upper arch 12 illustrated in FIG. 1b or any other suitable mold of one or more of the user's teeth.

A deformable material 32 is introduced into the region between outward surface 17 and first mold 28 from any suitable source or delivery device 40, for example, and not by way of limitation, a syringe, hypodermic needle, hot glue gun, or other suitable delivery device. Deformable material 32 may be placed in a deformable state before, during or after deformable material 32 is placed in or becomes contained by delivery device 40. In one embodiment, deformable material 32 is placed in delivery device 40, placed in a liquid, melted, or other deformable state, and delivered to a selected region of upper arch 12 to reline first mold 28. Deformable material 32 couples to first mold 28 and wholly or partially fills the region between first mold 28 and the outward surface 17 of tooth 16. As a result, first offset 30 is reduced or eliminated, yielding a relined or customized dental device 11 that more optimally fits one or more of the user's teeth. Deformable material 32 may be delivered to upper arch 12 and may couple to or otherwise combine with first mold 28 while deformable material 32 is in a liquid, melted, or other deformable state.

In one embodiment, deformable material 32 includes one or more of the polycaprolactone polymers or other aliphatic polyesters discussed above. Deformable material 32 may also include another polymer or any other suitable mixture, compound, composition, or material, depending on the application. The present invention contemplates using a polycaprolactone polymer or other aliphatic polyester in any suitable dental or other application for which delivery of a deformable material to a selected region using a syringe, hypodermic needle, hot glue gun, or other suitable delivery device is necessary or desirable. As discussed above, deformable material 32 may cool and harden or otherwise take a more permanent shape relatively slowly and display increased thermoplasticity during cooling, compared to materials such as ELVAX. This may provide the user or clinical professional with additional time to properly conform deformable material 32 to the shape of the user's teeth.

In one embodiment, although deformable material 32 wholly or partially surrounds tooth 16 and couples to first mold 28 while deformable material 32 is in a liquid or melted state, the user experiences little or no discomfort when deformable material 32 is delivered. This is due to a variety of factors, taken separately or in combination. First, since deformable material 32 includes a polycaprolactone polymer, alone or together with any other suitable material, deformable material 32 may transfer relatively little heat to tooth 16 and the tissues of the user's mouth. Second, since deformable material 32 is delivered in a relatively thin layer to a selected region of upper arch 12, the volume of material transferring heat to tooth 16 and the tissues of the user's mouth is relatively small. Therefore, the user's mouth may absorb the heat transferred from deformable material 32 with little or no discomfort. Third, the user's teeth and the tissues of the user's mouth are generally well-adapted to exposure to hot substances, for example, hot food and liquids. The present invention contemplates other factors that may also contribute to the user experiencing little or no discomfort when deformable material 32 is introduced into device 11.

As shown in FIG. 2b, deformable material 32 couples to first mold 28 and forms a second mold 36 of tooth 16. In one embodiment, deformable material 32 mixes, reacts, or otherwise combines with deformable material 21 to form second mold 36. A second offset 34 indicates the thickness of the space, if any, between second mold 36 and the outward surface 17 of tooth 16. Although deformable material 32 may have a tendency to contract as it cools, second offset 34 is smaller than first offset 30. As a result, second mold 36 conforms to the shape of tooth 16 more optimally than did first mold 28. This is due, at least in part, to the dimensional stability displayed by the polycaprolactone polymers as deformable material 32 cools, which reduces the contraction of deformable material 32 during the cooling process.

As indicated by the dashed lines 39, upper arch 12 or lower arch 14 may remain inserted in the user's mouth or may be removed from the user's mouth before, during, or after deformable material 32 cools or otherwise hardens to form second mold 36. Once second mold 36 is formed, upper arch 12 may be repeatedly removed and reinserted into the user's mouth as appropriate for the treatment or other use for which device 11 was constructed. Furthermore, upper arch 12 may be coupled to lower arch 14, a mask, or other apparatus in some suitable manner to form a device suitable for preventing trauma injuries or treating breathing problems such as sleep apnea. Relined dental devices and methods are claimed and described in copending applications Ser. Nos. 08/621,133 and 08/653,285, both of which are herein incorporated by reference.

Figure 3A:
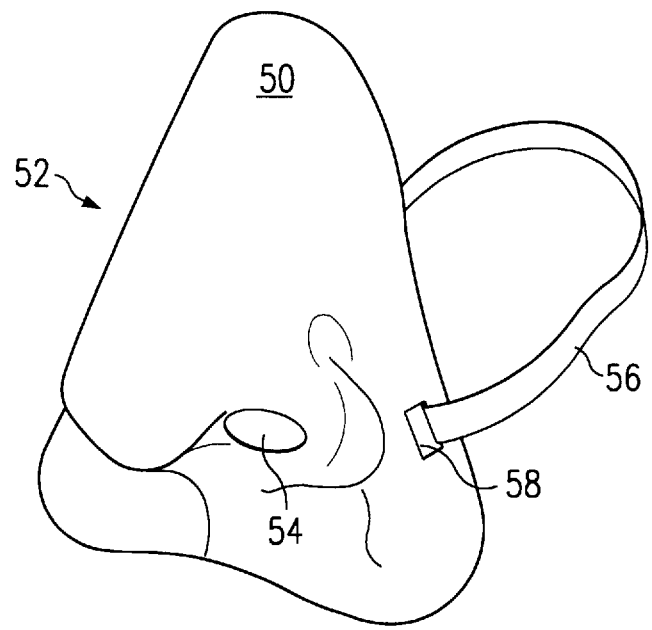
FIGS. 3a and 3b illustrate masks having an improved deformable material.

FIG. 3a illustrates a deformable material 50 that has been conformed to the shape of at least a portion of a user's face to form a mask 52. In one embodiment, deformable material 50 includes one or more of the polycaprolactone polymers discussed above, and may also include other polycaprolactone or other polymers or any other suitable material. Deformable material 50 is placed in its deformable state, delivered to a selected region of the user's face using a syringe, hypodermic needle, hot glue gun, or other suitable delivery device, and spread over at least a portion of the surface of the user's face so as to conform to the shape of the user's face over one or more contact regions. Straws or other breathing tubes may be inserted into the nostrils of the user beforehand, so that breathing channels 54 are formed in mask 52 when deformable material 50 cools or otherwise hardens to form mask 52. Because deformable material 50 includes one or more polycaprolactone polymers, deformable material 50 may cool relatively slowly, have increased thermoplasticity during cooling, and display increased dimensional stability during cooling, compared to materials such as LEXAN or ELVAX.

Mask 52 may be coupled to strap attachment 58 and strap 56 to allow the user to secure mask 52 about the user's head. a continuous positive air pressure (CPAP) device may be attached to mask 52 in some suitable manner, for example, using a deformable material that includes one or more polycaprolactone polymers or any other suitable material, to deliver a gas to the user's nose. Mask 52 may be coupled to any dental or other suitable device designed to prevent trauma injuries or treat breathing problems such as sleep apnea. The present invention contemplates using mask 52 in any suitable manner, whether or not mask 52 is coupled to a dental or other device.

Figure 3B:
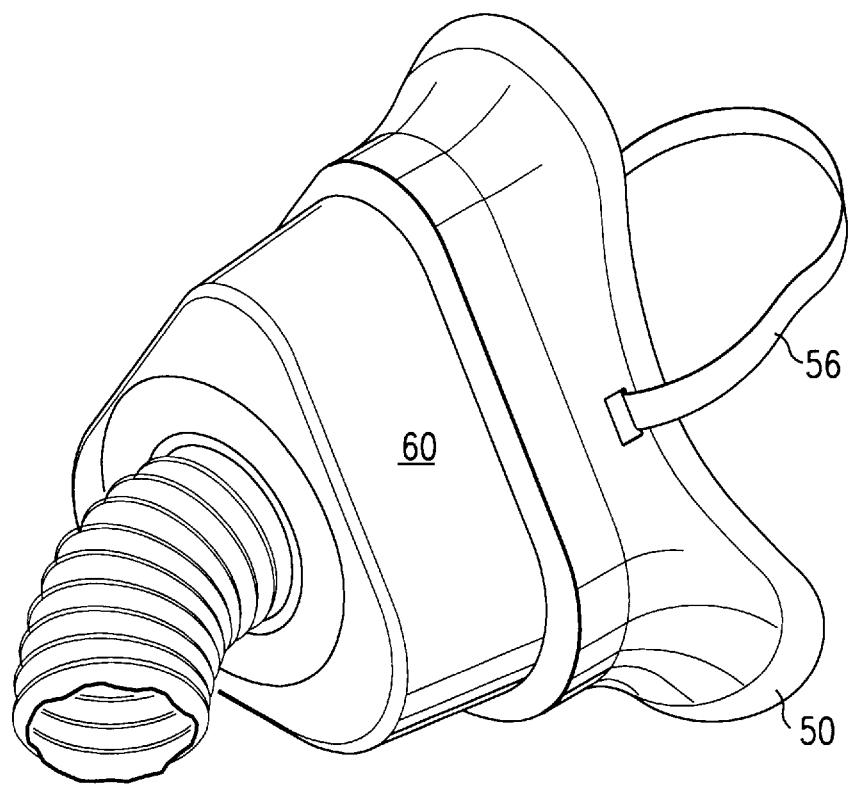

As shown in FIG. 3b, deformable material 50 may be used to customize an existing mask 60 for a particular user. Deformable material 50 is placed in a deformable state and delivered to mask 60, using a syringe, hypodermic needle, hot glue gun, or other suitable delivery device, around at least a portion of the perimeter of mask 60 so as to conform to the shape of the user's face. In one embodiment, polyvinyl siloxane may replace or combine with deformable material 50 to customize mask 52 or mask 60 for a particular user. For example, polyvinyl siloxane may be formed around at least a portion of the perimeter of mask 52 or mask 60, as the case may be, so as to conform to the shape of the user's face. The polyvinyl siloxane may be coupled to deformable material 50 after deformable material 50 has been used to customize mask 60. The present invention contemplates forming or customizing a mask in any suitable manner using one or more polycaprolactone polymers.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A method for customizing a dental device using an improved deformable material and subsequently inserting the customized dental device into a user's mouth, the method comprising:

inserting an arch into a user's mouth, the arch operable to receive at least one of the user's teeth, the arch comprising a first mold of the tooth that is separated from the tooth by a first offset;

delivering the deformable material to a selected region of the arch while the arch is inserted in the user's mouth to customize the dental device for the user, the deformable material comprising an aliphatic polyester;

forming a second mold of the tooth with the deformable material to customize the dental device, the second mold being separated from the tooth by a second offset that is smaller than the first offset; and inserting the customized dental device, including the arch and the deformable material, into the user's mouth to perform a function selected from the group consisting of:

preventing injury; and treating a breathing disorder.

2. The method of claim 1, further comprising the step of coupling the deformable material to the arch while the arch is in the user's mouth to customize the dental device.

3. The method of claim 1, further comprising the step of forming a mold of one or more of the user's teeth while the arch is in the user's mouth to customize the dental device.

4. The method of claim 1, wherein the deformable material is delivered to the arch while the deformable material is in a liquid state.

5. The method of claim 1, wherein the aliphatic polyester comprises a first polycaprolactone polymer.

6. The method of claim 1, wherein the aliphatic polyester has the formula:

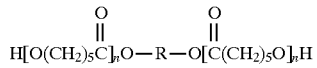

wherein R is an aliphatic hydrocarbon.

7. The method of claim 1, wherein the aliphatic polyester comprises a homopolymer of caprolactone initiated with a diol.

8. The method of claim 1, further comprising the step of combining a second polymer with the aliphatic polyester to form the deformable material.

9. The method of claim 8, wherein the second polymer is a second polycaprolactone polymer.

10. The method of claim 1, wherein the deformable material is delivered using a syringe.

11. The method of claim 1, wherein the deformable material is delivered using a hypodermic needle.

12. The method of claim 1, wherein the deformable material is delivered using a hot glue gun.

* * * * *